United States Patent [19]
Tam

[11] Patent Number: 5,461,651
[45] Date of Patent: Oct. 24, 1995

[54] RECONSTRUCTION OF IMAGES IN CONE BEAM SCANNING WITH RECTANGULAR DETECTOR ELEMENTS

[75] Inventor: Kwok C. Tam, Schenectady, N.Y.

[73] Assignee: General Electric Company, Schenectady, N.Y.

[21] Appl. No.: 153,504

[22] Filed: Nov. 17, 1993

[51] Int. Cl.$^6$ ............................. A61B 6/03; G01N 23/08
[52] U.S. Cl. .............................. 378/4; 378/19; 378/901; 364/412.13; 364/413.19
[58] Field of Search ..................... 364/413.13, 413.14, 364/413.15, 413.16, 413.19; 378/4, 19, 901

[56] References Cited

U.S. PATENT DOCUMENTS

| | | | |
|---|---|---|---|
| 4,159,424 | 6/1979 | Kingsley | 250/483.1 |
| 4,870,279 | 9/1989 | Cueman et al. | 250/368 |
| 4,920,491 | 4/1990 | Eberhard et al. | 364/413.19 |
| 4,958,282 | 9/1990 | Barjhoux | 364/413.13 |
| 5,032,990 | 7/1991 | Everhard et al. | 364/413.15 |
| 5,053,958 | 10/1991 | Tam | 364/413.13 |
| 5,068,882 | 11/1991 | Eberhard | 378/4 |
| 5,073,910 | 12/1991 | Eberhard et al. | 378/4 |
| 5,257,183 | 10/1993 | Tam | 364/413.19 |
| 5,341,460 | 8/1994 | Tam | 395/119 |

OTHER PUBLICATIONS

"An Inversion Formula for Cone–Beam Reconstruction", Heang K. Tuy, Siam J. Appl. Math., vol. 43, No. 3, Jun 1983, pp. 546–552.
"Convolutional Reconstruction from Cone–Beam Projection Data," Minerbo, IEEE Transaction on Nuclear Science, vol. NS–26, No. 2, Apr. 1979, pp. 2682–2684.
"Practical Cone–Beam Algorithm", Feldkamp et al., J. Opt. Soc. Am. A/vol. 1, No. 6, Jun. 1984, pp. 612–619.
"Iterative Three–Dimensional Reconstruction from Twin–Conbe Beam Projections", Schlindwein, IEEE Transactions on Nuclear Science, vol. NS–25, No. 5, Oct. 1978, pp. 1135–1143.
"Cone–Beam Tomography: Recent Advances and Tutorial Review", Smith, Optical Engineering, May 1990, vol. 29, No. 5, pp. 524–534.
"Image Reconstruction from Cone–Beam Projections: Necessary and Sufficient Conditions and Reconstruction Methods", Smith, IEEE Transactions on Medical Imaging, vol. MI–4, No. 1, Mar. 1985, pp. 14–25.
"Quantitative Cone–Beam Reconstruction", Hui Hu, Kruger, et al., SPIE vol. 1092 Medical Imaging III: Image Processing (1989), pp. 492–501.
"Analysis of a 3D Imaging System by Reconstruction from X Radiographies in Conbical Geometry", Doctoral Thesis by Pierre Grangeat, pp. 1–303.

Primary Examiner—David P. Porta
Assistant Examiner—David Vernon Bruce
Attorney, Agent, or Firm—Paul R. Webb, II

[57] ABSTRACT

Computerized tomography (CT) reconstruction of images is accomplished for asymmetric grids. After initial data acquisition and normalization, the asymmetric projection data is distorted by a compression process which effectively converts the data into symmetric data. The data may then be processed using Radon reconstruction procedures which convert projection data into object density functions. The object density functions or data which are provided are then subject to a stretching or extension procedure which compensates or reverses the initial distortion or compression. Cone beam imaging with asymmetric grids may be two-dimensional or three dimensional when utilizing the technique.

26 Claims, 7 Drawing Sheets

RECONSTRUCTION OF IMAGES IN CONE BEAM SCANNING WITH RECTANGULAR DETECTOR ELEMENTS

CROSS REFERENCE TO RELATED APPLICATIONS

The invention disclosed and claimed herein is related to the subject matter of the following commonly-assigned patent applications, the entire disclosures of which are hereby incorporated by reference:

Ser. No. 07/631,818, filed Dec. 21, 1990, invented by Kwok C. Tam, now abandoned, entitled "PARALLEL PROCESSING METHOD AND APPARATUS FOR RECONSTRUCTING A THREE-DIMENSIONAL COMPUTERIZED TOMOGRAPHY (CT) IMAGE OF AN OBJECT FROM CONE BEAM PROJECTION DATA OR FROM PLANAR INTEGRAL";

Ser. No. 07/631,815, filed Dec. 21, 1990, in the name of Kwok C. Tam, now U.S. Pat. No. 5,257,183, entitled "METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT", now U.S. Pat. No. 5,257,183; and Ser. No. 08/100,818, filed Aug. 2, 1993, in the name of Kwok C. Tam, Entitled "TOMOGRAPHY WITH GENERATION OF RADON DATA ON POLAR GRID POINTS".

BACKGROUND OF THE INVENTION

The present invention relates generally to imaging using cone beam scanning. More specifically, it relates to such tomographic imaging using asymmetric grids corresponding to non-square rectangular or other non-square detector elements.

In conventional computerized tomography (CT) for both medical and industrial applications, an x-ray fan beam and a linear array detector are used. Two-dimensional (2D) imaging is achieved. While the data set may be complete and image quality is correspondingly high, only a signal slice of an object is imaged at a time. When a 3D image is required, a stack of slices approach is employed. Acquiring a 3D data set one 2D slice at a time is inherently slow. Moreover, in medical applications, motion artifacts occur because adjacent slices are not imaged simultaneously. Also, dose utilization is less than optimal because the distance between slices is typically less than the x-ray collimator aperture, resulting in double exposure to many parts of the body. In 2D CT, the scanning path of the source is often a simply circular scan about the object. The linear array detector is fixed relative to the source. (Although it is usually to talk about a scan path of a source relative to the object to be imaged, it is to be appreciated that the object may be rotated or otherwise moved to provide relative motion between the object and the source.)

In a system employing true cone beam geometry for 3D imaging, a cone beam x-ray source and a 2D area detector are used. An object is scanned, preferably over a 360° angular range, either by moving the x-ray source in a scanning circle about the object or by rotating the object while the source remains stationary. In either case, the area detector is fixed relative to the source. The relative movement between the source and object which is to be imaged provides scanning in either case. Compared to the conventional 2D stack of slices approach to achieve 3D imaging, the cone beam geometry has the potential to achieve rapid 3D imaging of both medical and industrial objects with improved dose utilization.

The 3D CT imaging generally uses a Radon transform approach. (Radon transforms are also used in 2D CT.) The object is defined in terms of its x-ray attenuation coefficient. The measured cone beam projection data corresponds to a line integral of this function over the radial direction from the radiation source to a particular detector element within the detector array. The 3D Radon transform of an object at a point is given by the area integral of the x-ray attenuation coefficient over the plane passing through the point, which plane is perpendicular to the line from the origin to the particular point. If parallel beams of x-rays are applied to the object which is to be imaged, line integrals of the detector data are equal to the Radon transform of the object. However, obtaining the Radon transform is significantly more complex where a cone beam of x-ray or other imaging energy is applied to the object. In that case, obtaining the Radon transform, also called Radon data, is significantly more difficult. Once Radon data is obtained, an inverse Radon transformation is used to convert the Radon data into a reconstructed image which is then displayed.

The present inventor's previous application U.S. Pat. No. 5,257,183, incorporated by reference above, discloses a technique for calculating the radial derivative of Radon data from cone beam data. The present inventor's incorporated by reference application Ser. No. 07/631,818 discloses a technique for inverting the Radon data to obtain the reconstructed image of the object which is being viewed. In order to perform the Radon inversion, Radon data (as opposed to derivatives of Radon data) is required (except where using those few processors which perform Radon inversion using derivative data) and the Radon data should reside on polar grids on a number of predetermined vertical planes containing the z axis as the common axis. These requirements arise because the first part of the Radon inversion process is a two dimensional (2D) CT image reconstruction on each vertical plane, which takes input data in the form of Radon data at equally spaced angle θ and equally spaced detector spacings s. However, the technique of the referenced 07/631,815 application initially produces radial derivatives of the Radon data, instead of Radon data itself, and the derivative data is generated on a spherical shell having as its diameter a line segment SO connection a source position S and an origin O (instead of being generated on the points of the polar grids). The U.S. Pat. No. 5,257,183 application further describes techniques for converting from the radial derivative of Radon data to Radon data itself and to obtain the Radon data on the polar grid points by use of the Radon data relative to the spherical shell, often called the Radon shell. However, the calculation of Radon data over the spherical Radon shell requires a relatively large amount of processing or computational power. Further, using that Radon data to provide Radon data at the points on the polar grid of the vertical planes requires relatively complex techniques which, in effect, involve interpolation of different data points on the Radon shell over the shell. This three-dimensional (3D) interpolation is relatively complex and accordingly requires large amounts of computational power.

The present inventor's previous application Ser. No. 08/100,818, incorporated by reference above, provides for the simplification of the generation of Radon data.

The three incorporated by reference applications generally provide techniques allowing reconstruction of images using projection data. However, these and other reconstruction techniques (whether used for two-dimensional imaging or three-dimensional imaging) generally encounter problems when applied to asymmetric grids such as correspond to non-square rectangular or other non-square detector elements. For example, rectangular detectors which are not square could be used to provide better resolution in one dimension than in another dimension, this commonly being advantageous in medical imaging of a patient.

The problems with use of asymmetric grids will be better understood by initially realizing that tomography involves reconstruction of images from data collected at a number of angles. Common image reconstruction procedures are designed with symmetric geometry in mind. In two-dimensional (2D) computerized tomography (CT) images are usually reconstructed on a square grid with square grid elements. With symmetric geometry the various operations in image reconstruction, notably backprojection, can be carried out in the same manner at all the angles, resulting in uniform image quality and ease of operation.

Some situations make asymmetric geometry advantageous. For example, it is sometimes desirable to image an object with slice thickness larger than the later resolutions when using three-dimensional CT. Under such circumstances, the detector elements used in the area detector are usually non-square rectangular in shape, with their lateral and vertical dimensions determined by the corresponding detector element resolutions. The asymmetric voxel (the rectangular box on the grid) dimensions and detector element dimensions introduce complications in the image reconstruction operations and potentially non-uniform image quality.

OBJECTS AND SUMMARY OF THE INVENTION

Accordingly, it is a primary object of the present invention to provide a new and improved tomography system and method.

A more specific object of the present invention is to provide computerized tomography without requiring large increases in computational power for handling asymmetric grids.

Yet another object of the present invention is to provide efficient tomography with use of an asymmetric grid.

Yet another object of the present invention is to provide a tomography technique which will provide relatively uniform image quality.

A still further object of the present invention is to provide tomography techniques which allow ready use of image reconstruction procedures from asymmetric geometry when utilizing asymmetric geometry with detector elements having shapes other than squares.

The above and other objects of the present invention which will become more apparent as the description proceeds are realized by a method of computerized tomography including generating imaging energy; passing the imaging energy through an object of interest; and using an array detector having non-square elements to detect the imaging energy as attenuated by passage through the object of interest to provide asymmetric projection data corresponding to an asymmetric grid in which at least a portion of the object of interest is disposed. As used herein, non-square elements shall include any element in a linear (one-dimensional) array since such arrays are considered to be infinitely thin lines as well as non-square elements in a 2D array. As used herein, an asymmetric grid has boxes which are not squares (2D CT) or cubes (3D CT). The asymmetric projection data is converted into distorted projection data which is symmetric corresponding to a symmetric grid. The distorted projection data represents projection data which would be obtained upon subjecting the portion of the object of interest to a distorting transformation which transforms the asymmetric grid into the symmetric grid. Distorted reconstructed image data is generated by application of Radon image reconstruction in symmetric geometry using the distorted projection data. The distorted reconstructed image data is converted into asymmetric reconstructed image data by correcting for distortions introduced by the converting from asymmetric projection data into distorted projection data. As used herein, symmetric refers to a grid (and data corresponding thereto) where the grid is made of squares (if two-dimensional) or cubes (if three-dimensional). Other grids (and data corresponding thereto) is asymmetric.

In a first embodiment the computerized tomography is three-dimensional, the asymmetric grid and the symmetric grid are both three-dimensional, and the asymmetric reconstructed image data represents a three-dimensional image. The elements of the detector are rectangles arranged in a two dimensional array. The asymmetric grid is made of voxels having two square faces and four non-square rectangular faces, each square face having sides of $\Delta x$ and a long side of each non-square rectangular having a length of $\Delta z$.

The conversion of asymmetric projection data into distorted projection data is accomplished by using the formula:

$$P'_{a,b} = \frac{\Delta z \cos\theta_{a,b}(P_{a,b})}{\Delta x \cos\theta'_{a,b}}$$

where $P'_{a,b}$ is distorted projection data at an element located at a column G and a row b of the detector, $P_{a,b}$ is asymmetric projection data at an element located at a column a and row b of the detector, $\theta_{a,b}$ is the angle between an xy plane and a ray of imaging energy striking an element located at a column a and row b of the detector, the xy plane corresponding to the x axis and a y axis perpendicular to the x axis, and $\theta'_{a,b}$ is the angle between the xy plane and the ray after subjecting the ray and the detector to the distortion transformation.

The converting of distorted reconstructed image data into asymmetric reconstructed image data is accomplished by multiplying distorted reconstructed image data by $\Delta x/\Delta z$. The asymmetric reconstructed image data is a larger data set than the distorted reconstructed image data.

In a second embodiment, the computerized tomography is two-dimensional, the asymmetric grid and the symmetric grid are both two-dimensional, and the asymmetric reconstructed image data represents a two-dimensional image. The elements of the detector are arranged in two perpendicular one dimensional arrays. The asymmetric grid comprises non-square rectangular pixels having edges of $\Delta x$ and long edges $\Delta z$.

The conversion of asymmetric projection data into distorted projection data in the second embodiment is accomplished by using the formula:

$$P'_{a,b} = \frac{\Delta z \cos\theta_{a,b}(P_{a,b})}{\Delta x \cos\theta'_{a,b}}$$

where $P'_{a,b}$ is distorted projection data at an element located at a column a and a row b of the detector, $P_{a,b}$ is asymmetric projection data at an element located at a column a and row b of the detector, $\theta_{a,b}$ is the angle between an xy plane and a ray of imaging energy striking an element located at a column a and row b of the detector, and $\theta'_{a,b}$ is the angle between the xy plane and the ray of imaging energy after subjecting the ray and the detector to the distortion transformation.

The converting of distorted reconstructed image data into asymmetric reconstructed image data in the second embodiment is accomplished by multiplying distorted reconstructed image data by $\Delta x/\Delta z$. The asymmetric reconstructed image data is a larger data set than the distorted reconstructed image data.

Both the first and second embodiments may include the step of displaying an image by use of the asymmetric reconstructed image data.

The system for computerized tomography of the present invention includes: a source of generating cone beam imaging energy and passing it through an object of interest; and a detector for detecting the cone beam imaging energy as attenuated by passage through the object of interest to provide cone beam data.

The detector is an array detector having non-square elements to detect the imaging energy as attenuated by passage through the object of interest to provide asymmetric projection data corresponding to an asymmetric grid in which at least a portion of the object of interest is disposed. Distortion means are provided for converting the asymmetric projection data into distorted projection data which is symmetric corresponding to a symmetric grid. The distorted projection data represents projection data which would be obtained upon subjecting the portion of the object of interest to a distorting transformation which transforms the asymmetric grid into the symmetric grid. Generation means generate distorted reconstructed image data by application of Radon image reconstruction in symmetric geometry using the distorted projection data. Conversion means are provided for converting the distorted reconstructed image data into asymmetric reconstructed image data by correcting for distortions introduced by the converting from asymmetric projection data. A display is operably connected to display an image using the asymmetric reconstructed image data.

BRIEF DESCRIPTION OF THE DRAWINGS

The above and other features of the present invention will be more readily understood when the following detained description is considered in conjunction with the accompanying drawings wherein like characters represent like parts throughout the several views and in which.

DETAILED DESCRIPTION

Figure 1:
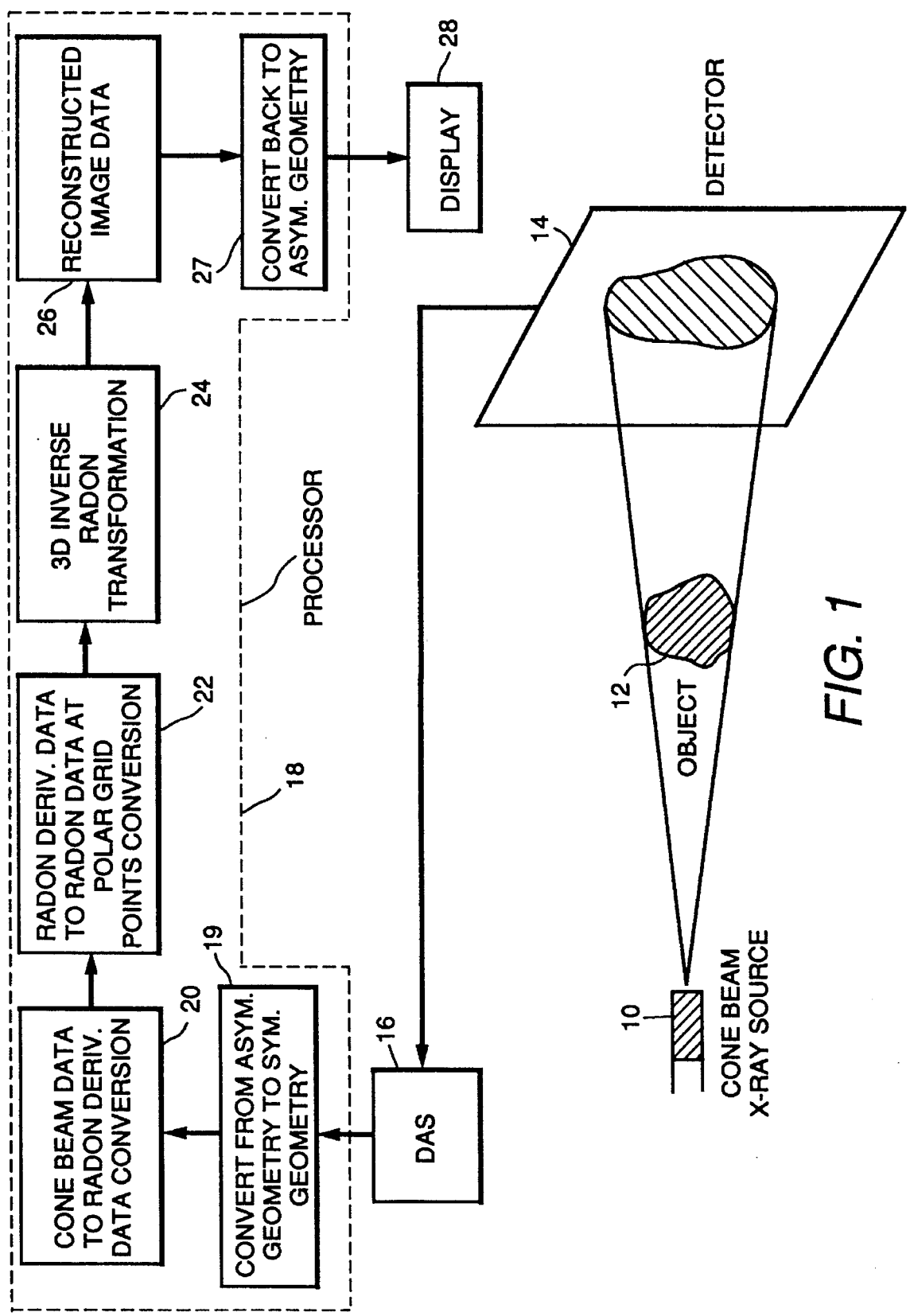
FIG. 1 is a simplified perspective of the imaging of an object using a source and detector and combined with a simplified block diagram of image reconstruction according to the present invention.

As shown in FIG. 1, a cone beam x-ray source 10 generates cone beam energy which passes through and about an object 12 which is to be imaged. Although source 10 is shown as an x-ray source, other types of imaging energy might be used. The imaging energy of whatever type is detected by detector 14. Although individual detector elements are not shown, it will be readily understood that the detector 14 is a two-dimensional array of individual detector elements. (Alternately, the detector could be two attached one-dimensional arrays of elements extending in two perpendicular single lines.) Relative movement between the source 10 and object 12 is used to provide more complete data about the object 12. For example, the object 12 could be rotated about a vertical axis (not shown) centered about the object 12. Alternately, and equivalently, the source 10 and detector 14 could be rotated about such an axis, while the object 12 remains stationary. Generally, the source 10 and detector 14 are fixed relative to each other. Additionally, the relative motion between the source 10 and object 12 may be more complex than a simple rotation as various techniques have been developed to ensure that a complete data set relative to the object 12 is obtained. Various other techniques provide supplementary data so as to provide reasonably accurate imaging even in cases of incomplete cone beam data. Both of those types of known techniques need not be described in detail for explaining the present invention.

Signals corresponding to the sensed x-ray energy falling on elements within the detector 14 are supplied to a data acquisition system 16 which, like the previously described portions of FIG. 1, may operate in known fashion.

Cone beam data from the data acquisition system 16 is supplied to a processor 18, which may be a computer programmed to perform various data conversions illustrated by the blocks within the processor 18. Block 19 converts projection data from a form corresponding to asymmetric data into a form corresponding to symmetric data, the details of which will be discussed below. Next, the cone beam data now in symmetric form is converted to Radon derivative data at block 20. This may be accomplished using the techniques described in the incorporated by reference application U.S. Pat. No. 5,257,183. The Radon derivative data is converted to Radon data at polar grid points at block 22 using a technique described in detail in the incorporated by reference application Ser. No. 08/100,818. The Radon data at the polar grid points is supplied to block 24 which performs an inverse 3D Radon transformation using the techniques described in detail in the incorporated by reference application Ser. No. 07/631,818. Blocks 20, 22, and 24 might be an image reconstruction process other than the Radon process.

The processor 18 supplies reconstructed image data at block 26 from the inverse Radon transformation of block 24. The image data of block 26 is fed into block 27 which converts data from a distorted symmetric form back into an asymmetric form, effectively reversing the image distortion introduced in block 19, in a manner described in more detail below. The asymmetric reconstructed data is fed from the processor 18 to a display 28, which may operate in known fashion to provide 3D CT imaging of the object 12.

The blocks of FIG. 1, other than blocks 19 and 27, are described in more detail in the incorporated by reference applications. Blocks 19 and 27, which are important features of the present invention, allow procedures for processing of symmetric data to be used for the processing of asymmetric data. Accordingly, the present application will concentrate on the details of blocks 19 and 27 after an explanation of principles used by the present invention.

Figure 2:
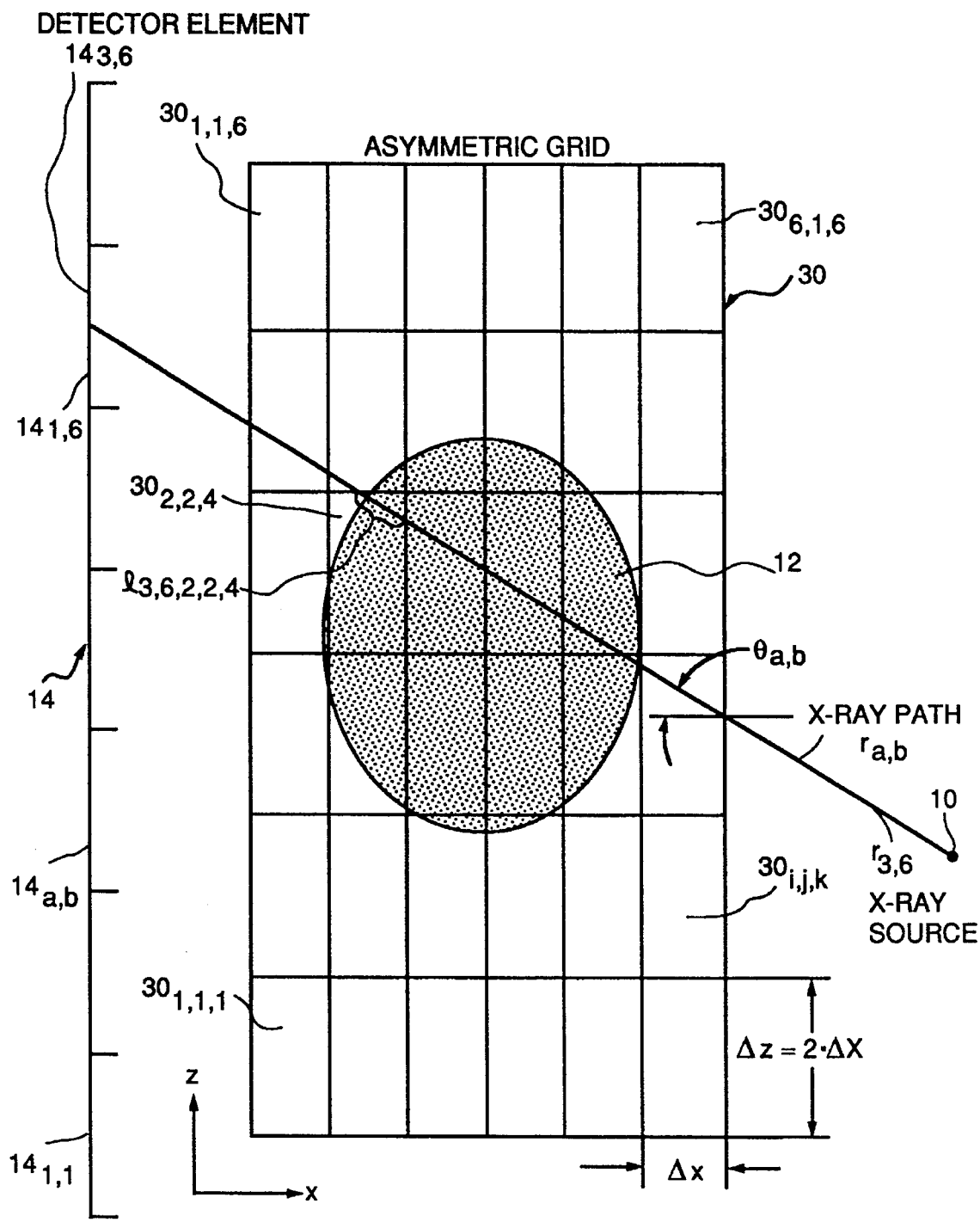
FIG. 2 shows a simplified side view of the source and detector with an asymmetric grid on the object of interest.
Figure 3:
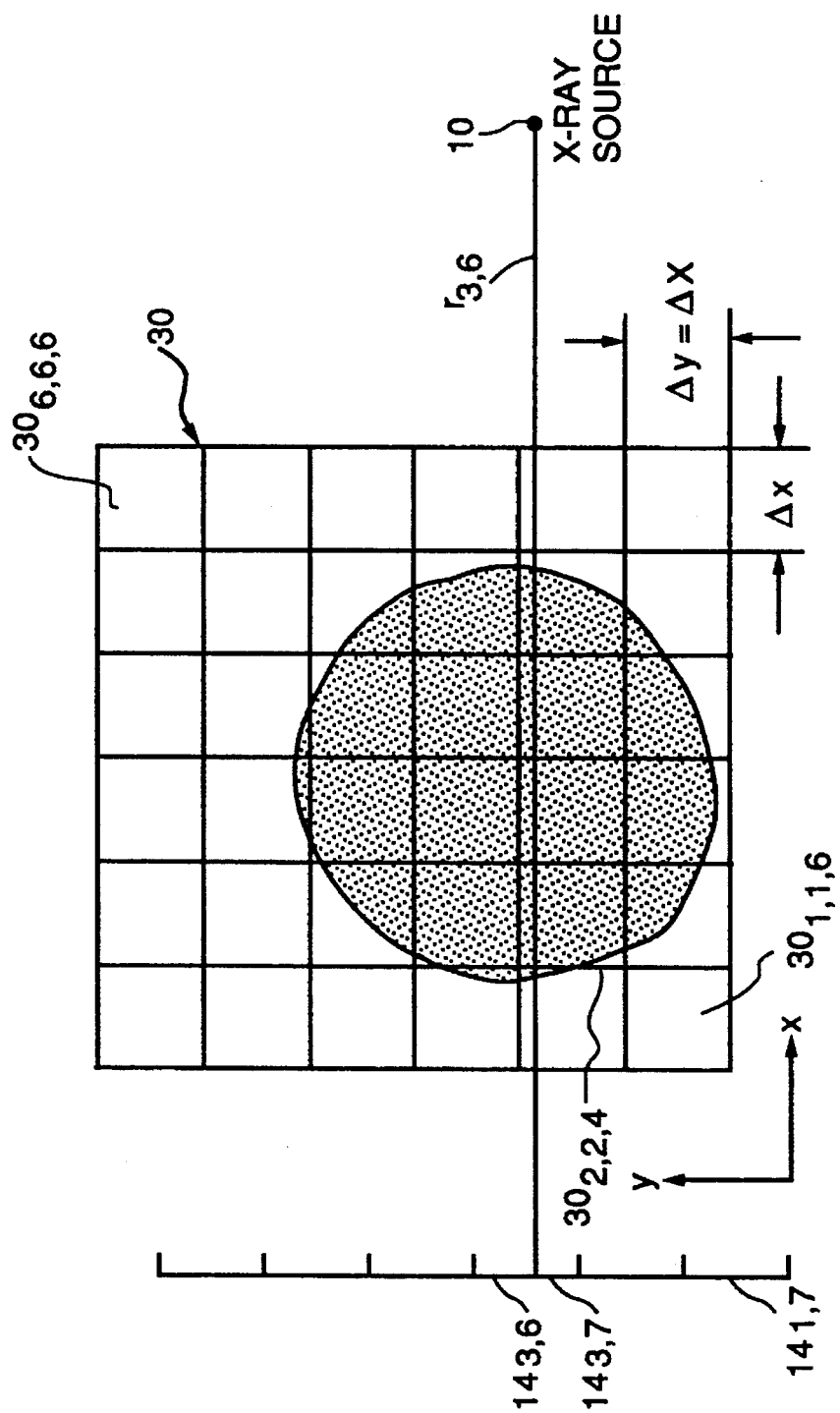
FIG. 3 shows a top view corresponding to FIG. 2.

With reference now to respective side and top simplified views of FIGS. 2 and 3, the detector 14 is a two-dimensional array having non-square rectangular detector elements $14_{a,b}$ separated by the hash marks and where a is an integer representing the column of the element (columns extending in the z direction with numbering starting at the bottom of FIG. 3) and b is an integer representing the row of the element (rows extending in the y direction with numbering starting at the bottom of FIG. 2). Corresponding to the asymmetric detector elements of detector 14 is an asymmetric grid 30 having a series of grid boxes $30_{i,j,k}$ with dimensions $\Delta x$, $\Delta y$, and $\Delta z$ where $\Delta x$, $\Delta y$, and $\Delta z = 2\Delta x$. The dimension of the grid boxes will result from the non-square elements of the detector 14. Integers i, j, and k respectively represent the location of the box relative to x, y, and z directions, several of the grid boxes being labeled for demonstrative purposes. It will be appreciated that the detector element $14_{3,6}$ is below a detector element $14_{1,6}$ (among other detector elements) in the view of FIG. 2 and detector elements $14_{3,6}$ is below detector element $14_{3,7}$ in the view of FIG. 3.

The discussion will assume that each of the boxes $30_{i,j,k}$ is a voxel having three dimensions. However, it will be readily understood that the same techniques and considerations would apply if FIG. 2 is simply considered as a top view of a two-dimensional imaging system wherein the boxes of grid 30 represent pixels. If FIG. 2 was considered as representing a top view of a two-dimensional imaging system, the array detector 14 would simply consist of a first line of coarse resolution detector elements arranged in a line parallel to the z axis of FIG. 2 and a second line (not shown) of detector elements having different resolution (finer resolution) than the first line elements. The second line is perpendicular to the second line and extends parallel to the x direction.

Whether FIG. 2 represents the top view of a two-dimensional imaging system or a vertical slice through a three-dimensional imaging system, it will readily be appreciated that the number of boxes within the grid and the number of detector elements within detector 14 would be significantly larger than the number illustrated. The relatively small number of detector elements and boxes within the grid 30 are illustrative without over complicating the views of FIGS. 2 and 3. The size of the detector elements of detector 14 are selected in order to provide the desired resolution, whereas the overall number of the detector elements are selected to provide the desired field of view. The size and number of the grid boxes within grid 30 depend upon the size and number of the detector elements within detector 14.

Consider an x-ray path $r_{a,b}$ from the x-ray source 10 to a detector element $14_{a,b}$. The projection data (after normalization) will be as follows:

$$P_{a,b} = \Sigma \rho_{i,j,k} l_{a,b,i,j,k} \quad (1)$$

where $P_{a,b}$ is the projection datum (after normalization) at detector element $14_{a,b}$, $P_{i,j,k}$ is the object density at grid box (voxel) $30_{i,j,k}$, and $l_{a,b,i,j,k}$ is the length of a segment of x-ray path $r_{a,b}$ within voxel $30_{i,j,k}$.

The summation of equation (1) above is carried out over the variables i, j, and k. It should be appreciated that this summation is effectively a line integral of the object density along the particular x-ray path $r_{a,b}$. The specific path shown is $r_{3,6}$. That path passes through voxel $30_{2,2,4}$ with a length therein as illustrated in FIG. 2 for demonstrative purposes. That length multiplied by the object density within the voxel contributes to the projection data received by detector element $14_{3,6}$.

It will be appreciated that the left side of equation (1) is readily provided by the elements of detector 14 after a simple, known normalization process. However, in order to reconstruct the image of the object 12, one must determine the object densities $\rho_{i,j,k}$. The procedure for obtaining those object densities (which are calculated from projection data for different relative positions of the source 10 and object 12 corresponding to the scanning movement of one relative to the other) uses blocks 20 thorugh 26 of FIG. 1 in a manner described in the three incorporated by reference patent applications. However, the asymmetric geometry corresponding to FIGS. 2 and 3 and the associated complications in the image reconstruction operations may cause non-uniform image quality.

Figure 4:
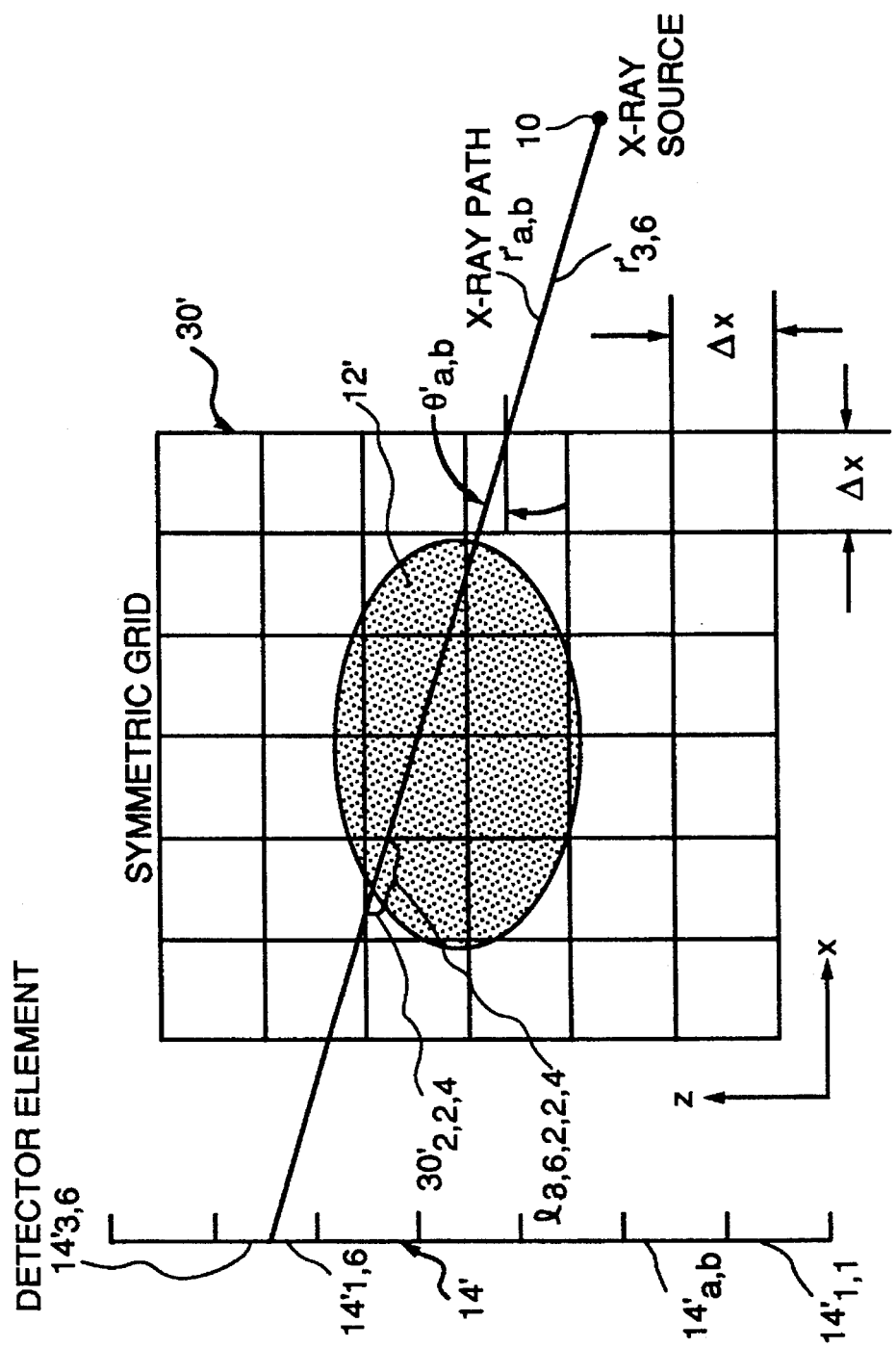
FIG. 4 shows the same side view as FIG. 2 after conversion to a symmetric grid.

FIG. 4 shows the same side view as FIG. 2 except where the z direction has been compressed using a distortion transformation, thus compressing the z dimensions of the detector elements, boxes within the grid, and object of interest. The deformed or compressed components of FIG. 4 are labeled with the same numerals as the corresponding components of FIG. 2, but with a prime ' added thereto. The z directions of FIG. 2 are compressed by multiplication by the ratio $\Delta x/\Delta z$ (where $\Delta x$ and $\Delta z$ are the voxel dimensions illustrated in FIG. 2). Although FIG. 2 has shown an example where $\Delta z$ is equal to twice the dimension of $\Delta x$ such that FIG. 4 would be obtained by simply multiplying the z dimensions by one half, this is simply an illustrative example and other asymmetric grids could be used. By compressing by the ratio $\Delta x/\Delta z$, the resulting grid 30' of FIG. 4 will be symmetric. Because the compression is uniform in the vertical or z dimension, the compressed x-ray path $r'_{3,6}$ will hit the same detector element $14'_{3,6}$ as in FIG. 2. (Element $14'_{3,6}$ is the same detector element as $14_{3,6}$.) Additionally, the relative geometry remains unchanged by the operation in that the x-ray path after compression crosses the same set of grid boxes before and after the compression. Further, the pattern of intersection with each grid box remains the same as is evident by comparing FIG. 4 to FIG. 2. FIG. 4 may be described by the following equation, which essentially corresponds to equation (1):

$$P'_{a,b} = \Sigma \rho'_{i,j,k} l'_{a,b,i,j,k} \quad (2)$$

where $P'_{a,b}$ is the projection datum (after normalization) at detector element $14'_{a,b}$, $\rho'_{i,j,k}$ is the object density at grid box (voxel) $30'_{i,j,k}$ and $l'_{a,b,i,j,k}$ is the length of a segment of x-ray path $r'_{a,b}$ within voxel $30'_{i,j,k}$.

Since the material with a box of grid 30 must equal the material within the corresponding box of grid 30', $$\rho_{i,j,k} \Delta x \Delta y \Delta z = \rho'_{i,j,k} \Delta x \Delta y \Delta x$$

which reduces to:

$$\rho'_{i,j,k} = \rho_{i,j,k} \Delta z / \Delta x \quad (3)$$

This equation shows the density change from the compression.

Since the segment length l within a particular voxel has the same x dimension ($\Delta x$) in FIGS. 2 and 4, $$l_{a,b,i,j,k} \cos\theta_{a,b} = l'_{a,b,i,j,k} \cos\theta'_{a,b}$$

which gives $$l'_{a,b,i,j,k} = l_{a,b,i,j,k} \cos\theta_{a,b} / \cos\theta'_{a,b} \qquad (4)$$

where $\theta_{a,b}$ and $\theta'_{a,b}$ are angles of respective corresponding original and compressed x-rays with respect to the xy plane (x axis in the 2D case) as shown in FIGS. 2 and 4, respectively. If the ray $r_{3,6}$ was not in the xz plane, FIG. 2 would have a plane of view different from the xz plane.

Substituting equations (1), (3), and (4) into equation (2) yields:

$$P'_{a,b} = \frac{\Delta z \cos\theta_{a,b}}{\Delta x \cos\theta'_{a,b}} \Sigma P_{a,b} l_{a,b,i,j,k}$$

which gives:

$$P'_{a,b} = \frac{\Delta z \cos\theta_{a,b}(P_{a,b})}{\Delta x \cos\theta'_{a,b}} \qquad (5)$$

The above relationship applies in the case of a 2D imaging system except that the b and k subscripts would not be present. In the 2D case, only rays hitting the vertical detector elements would be compressed.

Although FIG. 3 has shown a ray $r_{3,6}$ which has a projection in the xy plane parallel to the x axis, equation (5) would be true even if the ray of FIG. 3 appeared at an angle relative to the x axis in the view of FIG. 3. Note that the angles used in equation (5) ($\theta_{a,b}$ from FIG. 2 and $\theta'_{a,b}$ from FIG. 4) are actually angles between the xy plane and the ray path.

Referring back momentarily to FIG. 1, block 19 within the processor 18 calculates the compressed or deformed projections $P'_{a,b}$ for each of the detector elements $14_{a,b}$. As will be readily understood, the projection data for each detector element will be calculated repeatedly as the relative scanning of source 10 and object 12 proceeds.

Figure 5:
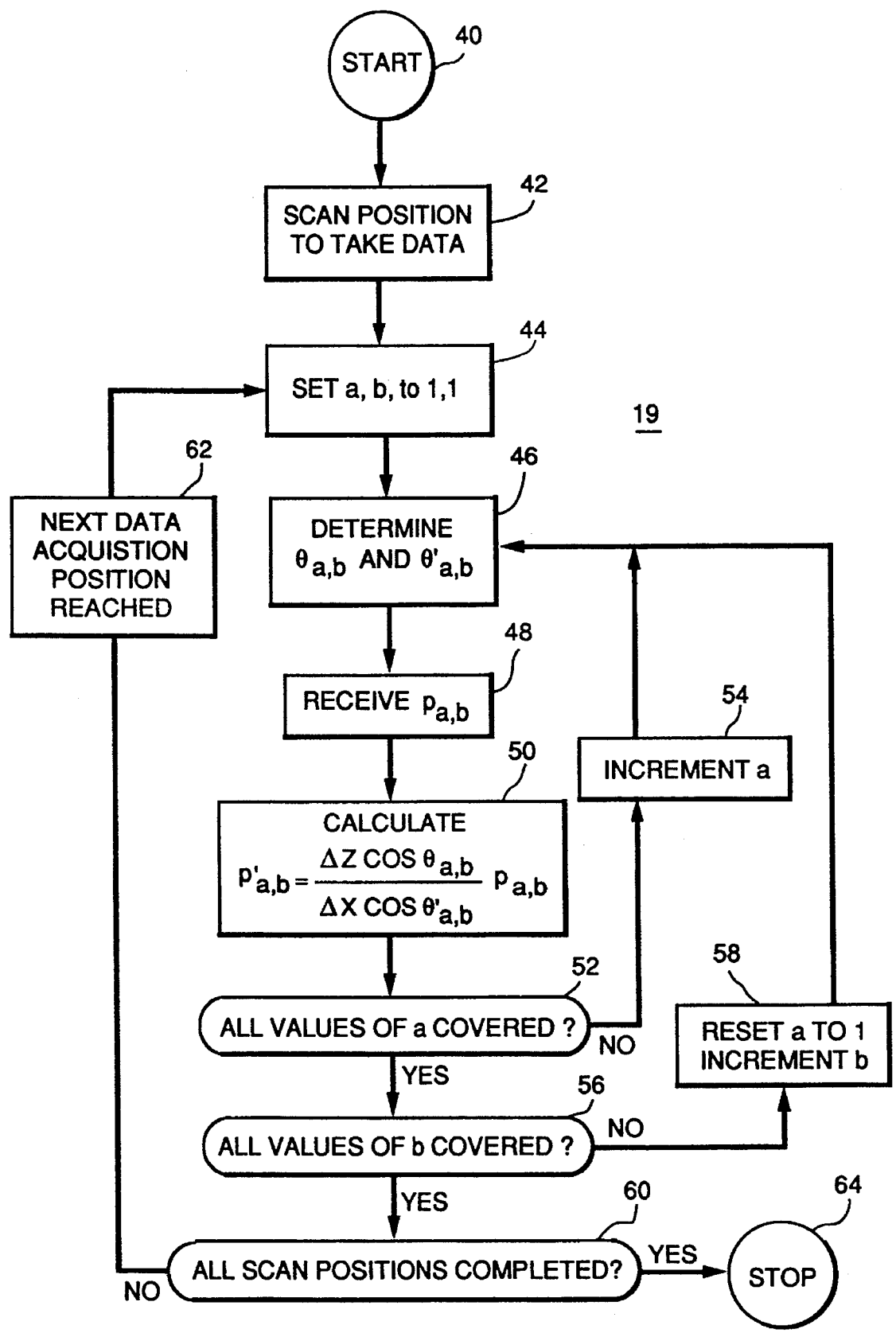
FIG. 5 shows a simplified flow chart of conversion from asymmetric projection data to distorted projection data.

Turning now to FIG. 5, there is shown a simplified flow chart illustrating the manner in which block 19 of FIG. 1 converts from asymmetric geometry data to symmetric geometry data. At start block 40, control proceeds to block 42 whereat the system assumes the scan position to take data. The scanning may be a continuous motion or a stepwise motion in known fashion. Block 42 simply indicates that the system has reached the initial data acquisition position. Block 42 transfers control to block 44 which initializes values for a and b at 1. Block 44 leads to block 46 which determines the angles used with equation 5 above. Those angles are shown in FIGS. 2 and 4 and may be readily calculated since the x,y,z coordinates of both the x-ray source 10 and the detector elements are known. Control transfers to block 48 where the normalized projection datum is received. This projection datum is then supplied to block 50 which actually performs equation (5), it being appreciated that $\Delta z$ and $\Delta x$ will have been previously known.

Block 50 leads to block 52 which determines if all of the values of a have been covered. If not, control returns to block 46 after incrementing a at block 54. If block 52 determines that all the values of G have been covered, this leads to block 56 which tests to determine if all the values of b have been covered. If not, control returns to block 46 after block 58 has reset a to 1 and has incremented b. In that fashion, all values of a and b will be covered.

If block 56 determines that all values of a and b have been covered, block 60 tests to determine if all scan positions have been completed. In other words, this tests to determine if all data acquisition positions have been completed. If not, control transfer back to block 44 by way of block 62 which simply indicates that the next data acquisition position has been reached. If block 60 determines that all scan positions have been completed, control transfers to block 64 which simply stops the process. Although not shown, the yes branch coming from block 56 might alternately lead directly to block 62 and blocks 60 and 64 could be deleted. In that case, the process would simply continue scanning the object of interest even after a complete scan had occurred. This is useful for observing patients or other objects of interest which change as time progresses.

Figure 6:
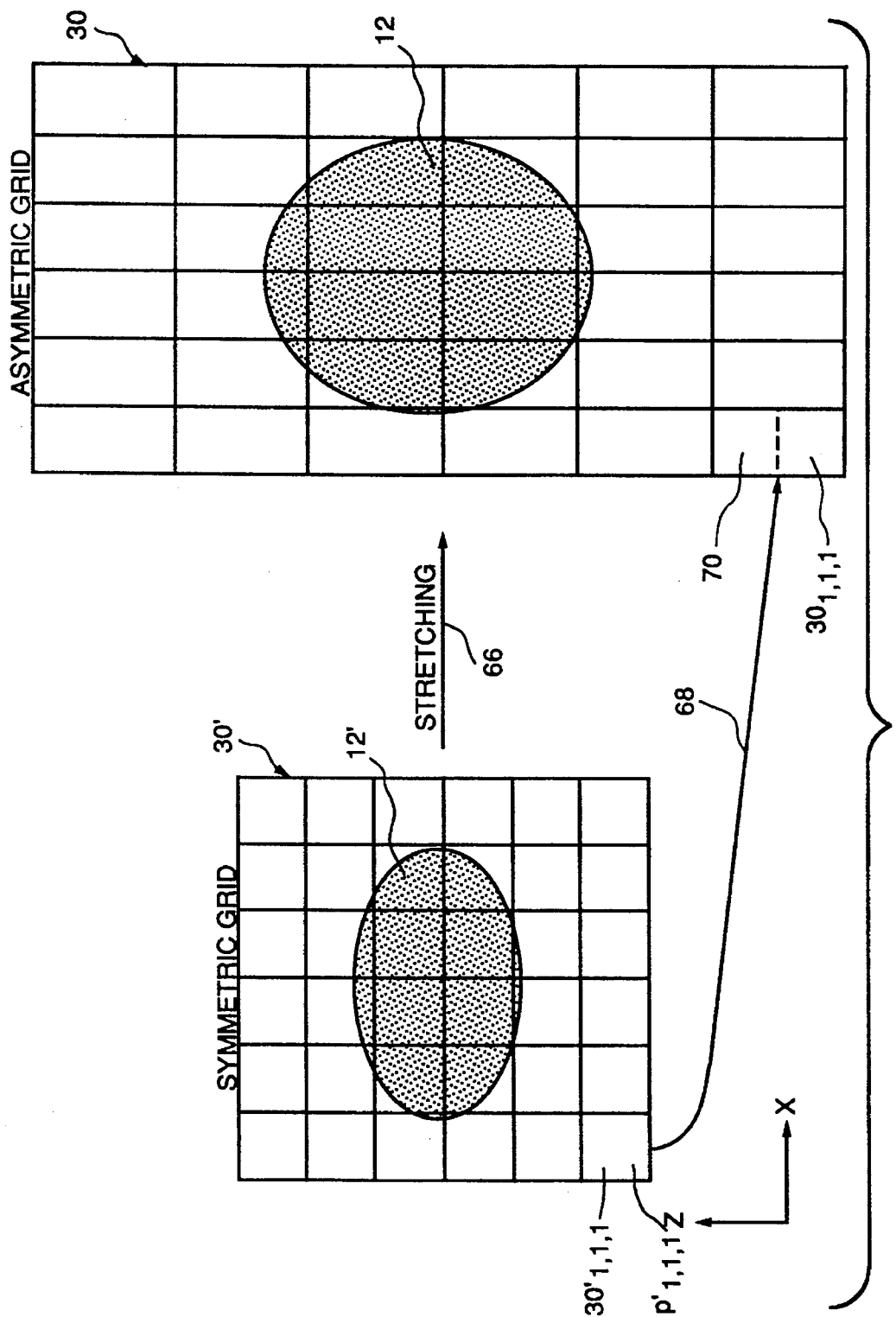
FIG. 6 shows in simplified fashion how reconstructed image data is converted back from asymmetric form to symmetric form.

Turning now to FIG. 6, the symmetric grid 30' and the asymmetric grid 30 are again illustrated with the respective compressed object 12' and original object 12. Referring back momentarily to FIG. 1, the data output from block 19 is processed through blocks 20, 22, 24, and 26 and output from block 26 to provide data in a form which may be illustrated schematically by the data within symmetric grid 30' at the left of FIG. 6. It will be recognized that the symmetric grid 30' at the left of FIG. 6 is identical to that shown in FIG. 4. However, it should be understood that when the symmetric grid 30' of FIG. 4 was discussed in connection with FIG. 4, it was illustrative of how projection data was obtained. Even though FIG. 4 showed the compressed object 12', this was for explanatory purposes only as one could not know of the distribution of the density function corresponding to object 12' until after the Radon process corresponding to blocks 20 through 26 of FIG. 1 was performed. Likewise, although the asymmetric grid 30 of FIG. 2 had the object 12 illustrated thereon for explanatory purposes, one could not know the shape of the object 12 (corresponding to the distribution of its density function) until after completion of the overall reconstruction process performed by processor 18 of FIG. 1. FIG. 6 simply indicates that a stretching, graphically shown by arrow 66, is performed to convert the density data corresponding to symmetric grid 30' (which density data is compressed or deformed) into asymmetric geometry data corresponding to the asymmetric grid 30. Conceptually, this stretching represented by arrow 66 is simply undoing the distortion or compression step which was performed to transform the FIG. 2 data into the FIG. 4 type of data discussed above. Taking the example where the vertical or z dimension was compressed by multiplying those dimensions by one half, the stretching 66 effectively multiplies the z dimension by two.

The stretching 66 will undo or reverse the distortions caused by compression of the object 12 into the distorted or compressed object 12'. Thus, and as shown at the right of FIG. 6, data corresponding to the original object 12 (more precisely its density function) will be available.

It should be noted that the undoing of the distortion of 12' to recover 12 is shown illustratively. Each of the boxes or voxels within grids 30' and 30 would have a uniform density function throughout that particular box. Thus, in order to accurately reflect the curvature in the object 12 (and in its distorted version 12'), a much larger number of boxes or voxels within the grids would be required with each of the boxes or voxels being relatively small compared to curves or other features on the object 12 which one wants to image. For ease of illustration, the drawings of the grids do not illustrate the hundreds or thousands of grid boxes which would be used in an actual case.

The stretching 66 of FIG. 6 may be accomplished in different ways.

A first and most simple way for accomplishing the stretching 66 is to use a display 28 (refer back momentarily to FIG. 1) which has pixels (not separately shown) having the same ratio of their z dimension to their x dimension as the grid boxes of asymmetric grid 30. Taking the example where the $\Delta z$ is twice the length of $\Delta x$ in the asymmetric grid 30 of FIG. 2, the display 28 would simply have pixels having a corresponding 2 to 1 ratio of height to width. In that case, the stretching 66 may be accomplished by simply taking the data corresponding to symmetric grid 30' and mapping each density value from a box in grid 30' into the corresponding box in grid 30 after multiplying the density value by $\Delta x/\Delta z$. Thus, the density function $\rho'_{1,1,1}$ at box $30'_{1,1,1}$ of grid 30' would be applied, after multiplication by $\Delta x/\Delta z$ in box 27 of FIG. 1, to the box $30_{1,1,1}$ of grid 30 as represented symbolically by the arrow 68. In the case of a display having asymmetric pixels corresponding to height to width ratios to those of asymmetric grid 30, the density function of a particular box within symmetric grid 30' would be mapped into an asymmetric grid 30 simply by having the data multiplied by $\Delta x/\Delta z$ and then supplied to the display 28.

A second way of performing the stretching 66 of FIG. 6 is illustrated symbolically by the dotted lines 70 in the middle of block $30_{1,1,1}$. In that case, the dotted lines 70 simply indicates that each of the pixels within the display 28 (display in FIG. 1, pixels not shown) corresponds to either the upper half or the lower half of one of the boxes within grid 30. In that case, and as represented symbolically by arrow 68, the density function from the corresponding box on symmetric grid 30' is mapped or supplied (after multiplication by $\Delta x/\Delta z$) into the two pixels within the display corresponding to that box. However, the density function (after multiplication) from the boxes within grid 30' is used to provide double (assuming $\Delta x/\Delta z$ is 2) the number of values within the array corresponding to grid 30. Assuming for example that only two-dimensional imaging is being performed, such that each of the boxes of 30' has a density value defining a 6 by 6 array, that array is mapped onto the asymmetric grid 30' to supply a 6 by 12 array with two of the entries in the asymmetric array corresponding to grid 30 corresponding to each one of the entries in the grid 30'.

Figure 7:
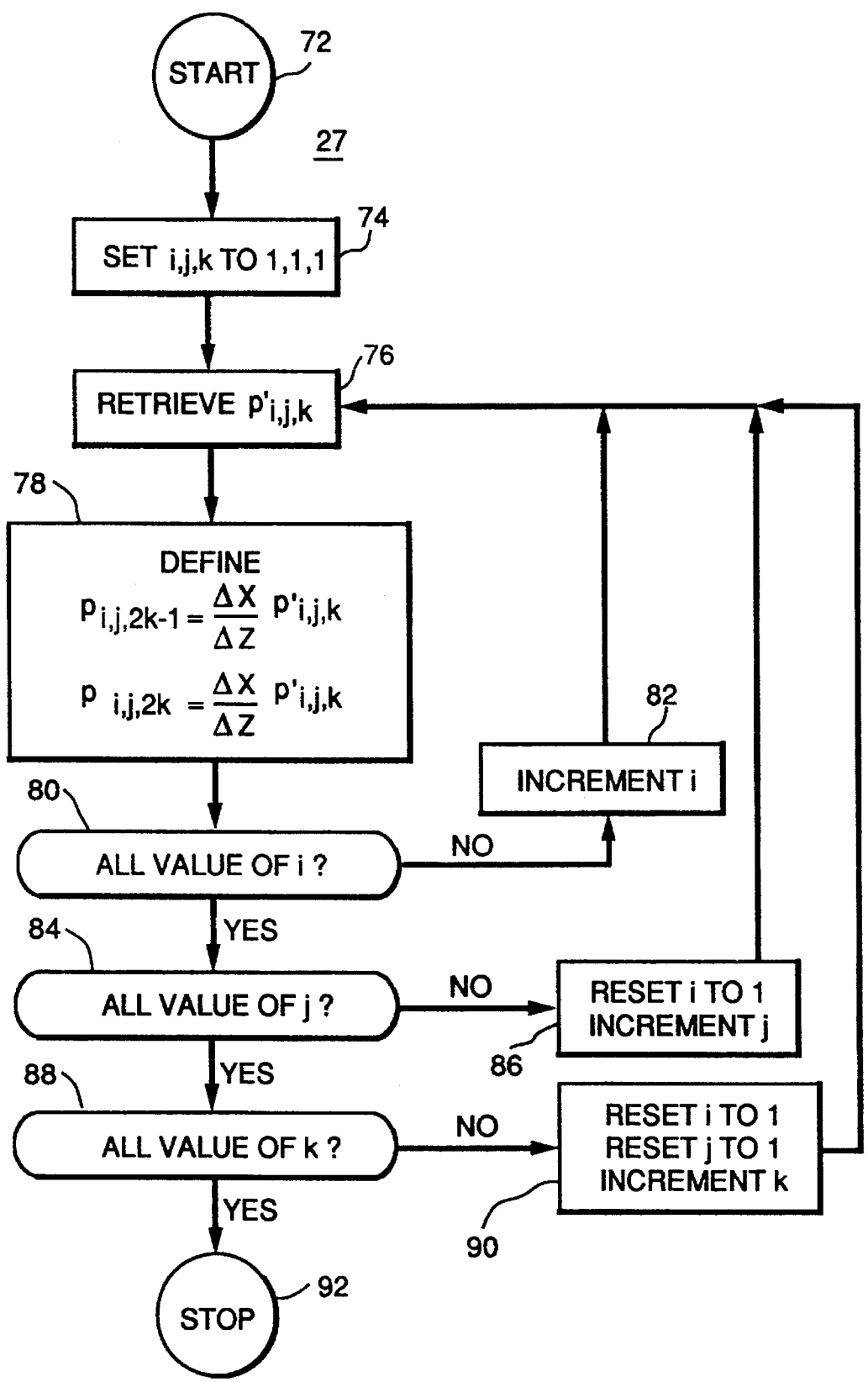
FIG. 7 shows a simplified flow chart of conversion from distorted reconstructed image data to asymmetric reconstructed image data.

Turning now to FIG. 7, a detailed explanation of a possible arrangement for block 27 will be presented. This detailed arrangement of FIG. 7 performs the stretching process discussed with respect to FIG. 6 by using the second technique wherein an array of the symmetric density functions (the array contains a component corresponding to the density function of each box within grid 30') is used to generate an array having twice as many components therein. Referring back momentarily to FIG. 6, the array which is generated by the FIG. 7 process corresponds to the grid 30. With reference back to FIG. 6, the process which will be described in FIG. 7 maps a density from a box in grid 30' to two array components corresponding to upper and lower halves of the corresponding box in grid 30. In this arrangement, the asymmetric grid 30, which depended from the elements in the detector 14, essentially has each of its boxes divided in half corresponding to the line 70 (illustrated only for one of the boxes). The upper half of each box is assigned the same density function as the lower half of the same box, both of these halves being assigned the density function from the corresponding box in the symmetric grid 30'.

The start 72 of process 27 of FIG. 7 transfers control to block 74 where index variables i,j,k are each set to a value of 1. Block 74 transfers control to block 76 whereat the compressed or distorted density function $\rho'$ for the particular values of i,j, and k is retrieved. Block 76 leads to block 78 where undistorted or uncompressed density functions $\rho$ are obtained using the distorted or compressed density functions (distorted reconstructed image data). The top equation of block 78 defines the undistorted density functions having an odd number as an index variable at its third subscripted value. In other words, this top equation defines the density function when its third index variable is an odd number. The second equation of block 78 defines the undistorted density function when the third index variable is an even number. It will be noted that the right side of both the upper and lower equations of block 78 are identical. Thus, and referring back momentarily to FIG. 6, the equations perform the function illustrated schematically by arrow 68 where the density function from one of the boxes in grid 30' is mapped, after multiplying by $\Delta x/\Delta z$, into both the upper and lower halves of a corresponding box in grid 30. If $\Delta x/\Delta z$ was 3, the density functions of grid 30' would be multiplied by ⅓ and mapped into 3 square or cube boxes of grid 30 such that block 78 would have three equations. Likewise, a $\Delta x/\Delta z$ of 4 would have multiplication by ¼ and so fourth for other ratios of $\Delta z$ to $\Delta x$.

Following block 78, block 80 tests to determine if the last value of i has been achieved. If not, control transfers back to block 76 by way of block 82 which increments i by 1, it being understood that any incrementing described in the present application would normally be by units of one unless stated otherwise. If block 80 determines that the last value of i has been used, control transfers to block 84 which tests for the last value of j and returns to block 76 by way of block 86 (incrementing j and resetting i to one) if the last value of j has not been reached. If the last value of j has been reached, control transfers to block 88 which tests to determine if the last value of k has been reached. If not, control returns to block 76 by way of block 90 (which increments k and resets both i and j to one). If the last value of k has been reached, control transfers to the stop block 92. Alternately, block 88 could lead back (not shown) to block 74 and the process could continue imaging over time to show motion of the object (such as a patient's heart).

Although the explanation of the stretching or conversion from symmetric distorted reconstructed image data to asymmetric undistorted reconstruction image data with respect to FIGS. 6 and 7 has been discussed primarily in terms of three dimensional grids 30' and 30, it will be readily understood that the same principle would be applicable to two dimensional grids which extend simply in the z and x directions of FIG. 6. In that case, the index variable j and corresponding blocks 84 and 86 could be deleted from the process of FIG. 7.

Although specific constructions and steps have been described herein, it is to be understood that these details are for illustrative purposes only. Various modifications and adaptations will be apparent to those of skill in this art. Accordingly, the scope of the present invention should be determined by reference to the claims appended hereto.

What is claimed is:

1. A method of computerized tomography comprising the steps of:

(a) generating imaging energy;

(b) passing the imaging energy through an object of interest;

(c) using an array detector having non-square elements to detect said imaging energy as attenuated by passage through the object of interest to provide asymmetric projection data corresponding to an asymmetric grid in which at least a portion of the object of interest is disposed;

(d) converting said asymmetric projection data into distorted projection data which is symmetric corresponding to a symmetric grid, said distorted projection data representing projection data which would be obtained upon subjecting said portion of said object of interest to a distorting transformation which transforms said asymmetric grid into said symmetric grid;

(e) Generating distorted reconstruction image data by application of image reconstruction in symmetric geometry using said distorted projection data; and (f) converting said distorted reconstructed image data into asymmetric reconstructed image data by correcting for distortions introduced by the converting from asymmetric projection data into distorted projection data.

2. The method of claim 1 wherein said computerized tomography is three-dimensional, said asymmetric grid and said symmetric grid are both three-dimensional, and said asymmetric reconstructed image data represents a three-dimensional image.

3. The method of claim 2 wherein said elements of said detector are rectangles arranged in a two dimensional array.

4. The method of claim 3 wherein said asymmetric grid comprises voxels having two square faces and four non-square rectangular faces, each square face having sides of $\Delta x$ and a long side of each non-square rectangular face having a length of $\Delta z$.

5. The method of claim 4 wherein said conversion of asymmetric projection data into distorted projection data is accomplished by using the formula:

$$P'_{a,b} = \frac{\Delta z \cos\theta_{a,b}(P_{a,b})}{\Delta x \cos\theta'_{a,b}}$$

where $P'_{a,b}$ is distorted projection data at an element located at a column a and row b of said detector, $P_{a,b}$ is asymmetric projection data at an element located at a column a and a row b of said detector, $\theta_{a,b}$ is the angle between an xy plane and a ray of imaging energy striking an element located at a column a and row b of said detector, the xy plane corresponding to said x axis and a y axis perpendicular to the x axis, and $\theta'_{a,b}$ is the angle between an xy plane and said ray after subjecting said ray and said detector to said distortion transformation.

6. The method of claim 5 wherein said converting of distorted reconstructed image data into asymmetric reconstructed image data is accomplished by multiplying distorted reconstructed image data by $\Delta x/\Delta z$.

7. The method of claim 6 wherein said asymmetric reconstructed image data is larger data set than said distorted reconstructed image data.

8. The method of claim 1 wherein said computerized tomography is two-dimensional, said asymmetric grid and said symmetric grid are both two-dimensional, and said asymmetric reconstructed image data represents a two-dimensional image.

9. The method of claim 8 wherein said asymmetric grid comprises non-square rectangular pixels having edges of $\Delta x$ and long edges $\Delta z$.

10. The method of claim 9 wherein said conversion of asymmetric projection data into distorted projection data is accomplished by using the formula:

$$P'_{a,b} = \frac{\Delta z \cos\theta_{a,b}(P_{a,b})}{\Delta x \cos\theta'_{a,b}}$$

where $P'_{a,b}$ is distorted projection data at an element located at a column a and row b of said detector, $P_{a,b}$ is asymmetric projection data at an element located at a column a and a row b of said detector, $\theta_{a,b}$ is the angle between an xy plane and a ray of imaging energy striking an element located at a column e and row b of said detector, and $\theta'_{a,b}$ is the angle between the xy plane and said ray of imaging energy after subjecting said ray and said detector to said distortion transformation.

11. The method of claim 10 wherein said converting of distorted reconstructed image data into asymmetric reconstructed image data is accomplished by multiplying distorted reconstructed image data by $\Delta x/\Delta z$.

12. The method of claim 11 wherein said asymmetric reconstructed image data is a larger data set than said distorted reconstructed image data.

13. The method of claim 1 further comprising the step of displaying an image by use of said asymmetric reconstructed image data.

14. The method of claim 1 wherein the generating of distorted reconstructed image data is by application of Radon image reconstruction.

15. A system for computerized tomography comprising:
   a source for generating cone beam imaging energy and passing it through an object of interest;
   a detector for detecting the cone beam image energy as attenuated by passage through the object of interest to provide cone beam data;
   (c) said detector being an array detector having non-square elements to detect said imaging energy as attenuated by passage through the object of interest to provide asymmetric projection data corresponding to an asymmetric grid in which at least a portion of the object of interest is disposed;
   (d) distortion means for converting said asymmetric projection data into distorted projection data which is symmetric corresponding to a symmetric grid, said distorted projection data representing projection data which would be obtained upon subjecting said portion of said object of interest to a distorting transformation which transforms said symmetric grid;
   (e) generation means for generating distorted reconstruction image data by application of image reconstruction in symmetric geometry using said distorted projection data; and
   (f) conversion means for converting said distorted reconstructed image data into asymmetric reconstructed image data by correcting for distortions introduced by the converting from asymmetric projection data into distorted projection data.

16. The system of claim 15 wherein said computerized tomography is three-dimensional, said asymmetric grid and said symmetric grid are both three-dimensional, and said asymmetric reconstructed image data represents a three-dimensional image.

17. The system of claim 16 wherein said elements of said detector are rectangles arranged in a two dimensional array.

18. The system of claim 17 wherein said asymmetric grid comprises voxels having two square faces and four non-square rectangular faces, each square face having sides of $\Delta x$ and a long side of each non square rectangular face having a length of $\Delta z$.

19. The system of claim 18 wherein said distortion means converts asymmetric projection data into distorted projection data by using the formula:

$$P'_{a,b} = \frac{\Delta z \cos\theta_{a,b}(P_{a,b})}{\Delta x \cos\theta'_{a,b}}$$

where $P'_{a,b}$ is distorted projection data at an element located at a column a and row b of said detector, $P_{a,b}$ is asymmetric projection data at an element located at a column a and a row b of said detector, $\theta_{a,b}$ is the angle between an xy plane and a ray of imaging energy striking an element located at a column a and row b of said detector, the xy plane corresponding to said x axis and a y axis perpendicular to the x axis, and $\theta'_{a,b}$ is the angle between the xy plane and said ray after subjecting said ray and said detector to said distortion transformation.

20. The system of claim 19 wherein said conversion means converts distorted reconstructed image data into asymmetric reconstructed image data by multiplying distorted reconstructed image data by $\Delta x/\Delta z$.

21. The system of claim 15 wherein said computerized tomography is two-dimensional, said asymmetric grid and said symmetric grid are both two-dimensional, and said asymmetric reconstructed image data represents a two-dimensional image.

22. The system of claim 21 wherein said asymmetric grid comprises non-square rectangular pixels having edges of $\Delta x$ and long edges $\Delta z$.

23. The system of claim 22 wherein said distortion means converts asymmetric projection data into distorted projection data by using the formula:

$$P'_{a,b} = \frac{\Delta z \cos\theta_{a,b}(P_{a,b})}{\Delta x \cos\theta'_{a,b}}$$

where $P'_{a,b}$ is distorted projection data at an element located at a column a and row b of said detector, $P_{a,b}$ is asymmetric projection data at an element located at a column a and a row b of said detector, $\theta_{a,b}$ is the angle between an xy plane and a ray of imaging energy striking an element located at a column a and row b of said detector, and $\theta'_{a,b}$ is the angle between the xy plane and said ray of imaging energy after subjecting said ray and said detector to said distortion transformation.

24. The system of claim 23 wherein said conversion means converts distorted reconstructed image data into asymmetric reconstructed image data by multiplying distorted reconstructed image data by $\Delta x/\Delta z$.

25. The system of claim 15 further comprising a display operatively connected to said conversion means for displaying an image based on said asymmetric reconstructed image data.

26. The system of claim 15 wherein said generation means for generating distorted reconstructed image data applies Radon image reconstruction.

* * * * *